(12) United States Patent
Hirohara et al.

(10) Patent No.: US 6,695,450 B2
(45) Date of Patent: Feb. 24, 2004

(54) OPHTHALMIC CHARACTERISTICS MEASURING APPARATUS

(75) Inventors: Yoko Hirohara, Tokyo (JP); Hirohisa Nakao, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 10/291,667

(22) Filed: Nov. 12, 2002

(65) Prior Publication Data

US 2003/0090627 A1 May 15, 2003

(30) Foreign Application Priority Data

Nov. 9, 2001 (JP) ........................................ 2001-344738
Sep. 25, 2002 (JP) ........................................ 2002-278295
Oct. 16, 2002 (JP) ........................................ 2002-301477

(51) Int. Cl.[7] ................................................ A61B 3/10
(52) U.S. Cl. ........................................ 351/211; 351/221
(58) Field of Search .............................. 351/205, 206, 351/211, 212, 221, 246; 356/121, 123

(56) References Cited

U.S. PATENT DOCUMENTS 6,299,311 B1 * 10/2001 Williams et al. ............ 351/221
6,582,079 B2 * 6/2003 Levine ........................ 351/221

FOREIGN PATENT DOCUMENTS

| JP | 11-028188 A | 2/1999 |
| JP | 2001-204690 A | 7/2001 |
| JP | 2002-125931 A | 5/2002 |

* cited by examiner

Primary Examiner—George Manuel
(74) Attorney, Agent, or Firm—Foley & Lardner (57) ABSTRACT

There is provided an ophthalmic characteristic measuring apparatus in which when a wavefront measurement is carried out, an adjustment of an exposure amount, such as an exposure time or a light amount of a light source, is carried out. A first light source section emits light flux with a first wavelength. A first illumination optical system illuminates a minute area on a retina of a subject eye with the first flux from the first light source. A first light receiving optical system guides a part of light flux reflected and returned from the retina of the subject eye to a first light receiving section through a first conversion member for converting the reflected light flux into at least 17 beams. A second light source section emits light flux with a second wavelength. A second illumination optical system illuminates a predetermined area on the retina of the subject eye with the second light flux from the second light source section. A second light receiving optical system guides the second light flux reflected and returned from the retina of the subject eye to a second light receiving section. An arithmetic section determines an exposure amount of the first light receiving section on the basis of a signal of the second light receiving section.

7 Claims, 10 Drawing Sheets

OPHTHALMIC CHARACTERISTICS MEASURING APPARATUS

BACKGROUND OF THE INVENTION

The present invention relates to an ophthalmic characteristic measuring apparatus.

As a conventional cornea shape measurement apparatus, an apparatus is known in which an index is projected on a subject eye, an imaging position of the index is obtained, and a cornea shape is measured. Besides, as an apparatus for measuring optical characteristics of an eye, in Japanese patent application assigned to the present assignee, an apparatus is disclosed in which a focus adjustment of an illumination optical system is carried out with a received light level measured through a Hartmann plate, and a focus adjustment of a light receiving optical system is carried out on the basis of optical characteristics (S) obtained from its received light output (see Japanese Patent Application No. 137630/1997).

However, in the conventional apparatus for measuring the optical characteristics of the subject eye, only correction of glasses can be carried out, and there has been a case where it can not be said that desired oohthalmic characteristics can be sufficiently measured. Besides, in the conventional ophthalmic characteristic measuring apparatus, there is a case where from a difference in the reflectivity of an eyeground intrinsic to each eye and in the transmittance of an eyeball optical system, each spot of a Hartmann image is saturated or the amount of light is insufficient, and it is difficult to precisely set an exposure amount, an exposure time or a light amount of a light source, and it is expected that it is difficult to measure accurate oohthalmic characteristics. Incidentally, in general, exposure amount=(exposure time×light amount of light source).

SUMMARY OF THE INVENTION

In view of the above, an object of the present invention is to provide an ophthalmic characteristic measuring apparatus which can adjust an exposure amount, such as an exposure time or a light amount of a light source, at the time of wavefront measurement.

According to the present invention, an ophthalmic characteristic measuring apparatus comprises a first light source section for emitting light flux with a first wavelength, a first illumination optical system for illuminating a minute area on a retina of a subject eye with the light flux from the first light source section, a first light receiving optical system for guiding a part of first reflected light flux reflected and returned from the retina of the subject eye to receive it through a first conversion member for converting the first reflected light flux into substantially at least 17 beams, a first light receiving section for receiving the received light flux of the first light receiving optical system to form a first signal, a second light source section for emitting light flux with a second wavelength, a second illumination optical system for illuminating an eyeground of the subject eye with the light flux from the second light source section and with a predetermined pattern, a second light receiving optical system for guiding second reflected light flux reflected and returned from the eyeground of the subject eye to receive it, a second light receiving section for receiving the received light flux of the second light receiving optical system to form a second signal, an arithmetic section for obtaining a wavefront of the light flux reflected from the subject eye on the basis of the first signal from the first light receiving section, and obtaining refractive power of the subject eye on the basis of the second signal from the second light receiving section, and an exposure amount determination section for determining an exposure amount of the first light receiving section on the basis of the second signal of the second light receiving section.

BRIEF DESCRIPTION OF THE DRAWINGS

FIG. 8 is a flowchart of a third embodiment showing a specific measurement method of the ophthalmic characteristic measuring apparatus 1000a.

FIG. 9 is a flowchart of a fourth embodiment showing a specific measurement method of the ophthalmic characteristic measuring apparatus 1000a.

DETAILED DESCRIPTION OF THE PREFERRED EMBODIMENTS

Hereinafter, embodiments of the present invention will be described in detail with reference to the drawings.

Figure 1:
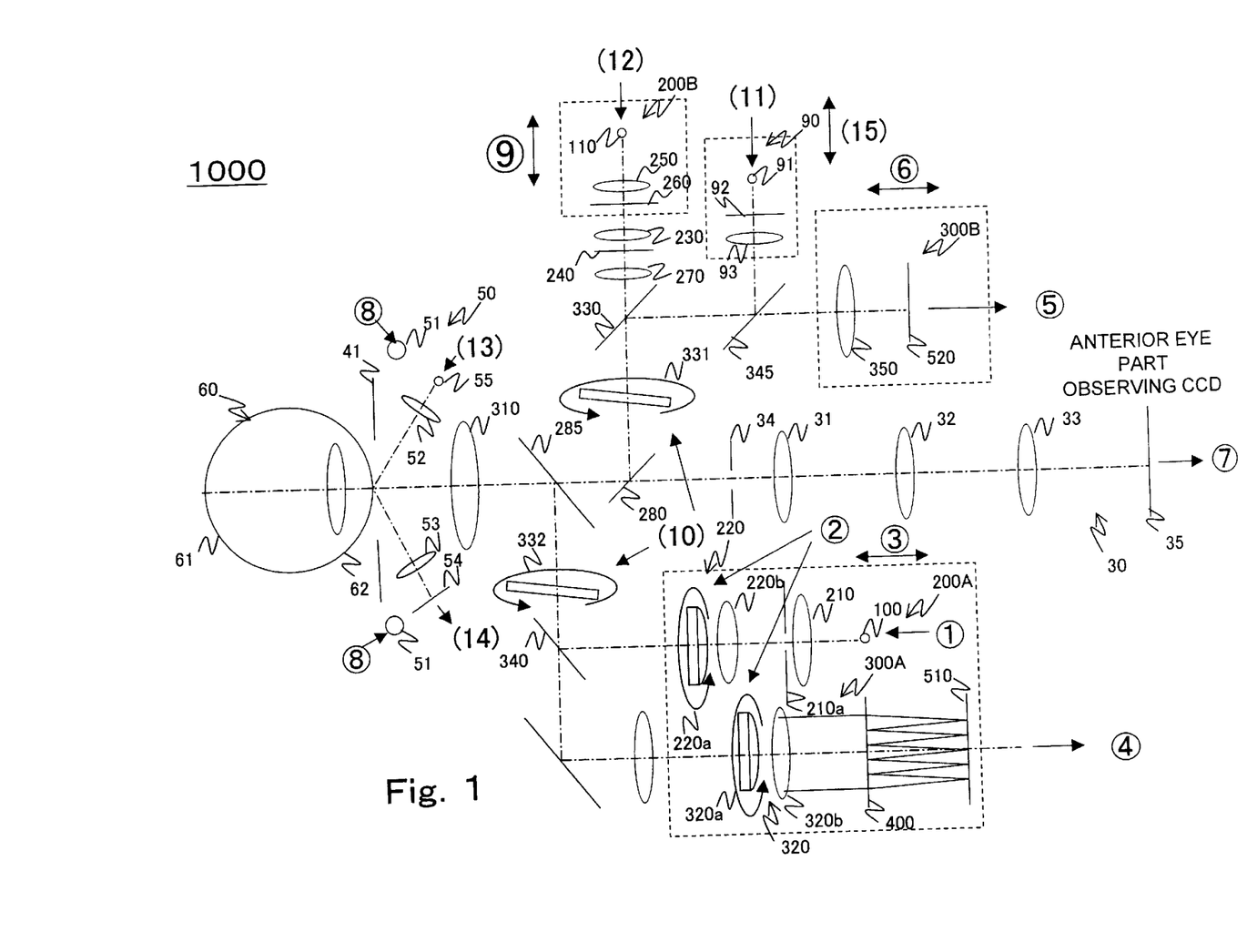
FIG. 1 is a view showing a general optical system of an ophthalmic characteristic measuring apparatus 1000 of the invention.

FIG. 1 is a view showing a general optical system of an ophthalmic characteristic measuring apparatus 1000 of the invention.

The ophthalmic characteristic measuring apparatus 1000 includes, for example, a first light source section 100, a first illumination optical system 200A, a first light receiving optical system 300A, a first light receiving section 510, a second light source section 110, a second illumination optical system 200B, a second light receiving optical system 300B, a second light receiving section 520, a third light source section 91, a third light receiving optical system 30, a first adjusting optical system 50, and a third illumination optical system 90. Incidentally, with respect to an eye 60 to be measured, a retina (eyeground) 61 and a cornea (anterior eye part) 62 are shown in the drawing.

The first light source 100 emits light flux with a first wavelength. The first illumination optical system 200A illuminates a minute area on the retina 61 of the subject eye with the first light flux from the first light source 100. The first light receiving optical system 300A guides a part of light flux reflected and returned from the retina 61 of the subject eye to the first light receiving section 510 through a first conversion member 400 for converting the reflected light flux into at least 17 beams. The second light source 110 emits light flux with a second wavelength. The second illumination optical system 200B illuminates a predetermined area on the retina 61 of the subject eye with the second light flux from the second light source 110. The second light receiving optical system 300B guides the second light flux reflected and returned from the retina 61 of the subject eye to the second light receiving section 520.

Hereinafter, the respective sections will be described in detail.

The first illumination optical system 200A is for illuminating a minute area on the retina 61 of the subject eye with the light flux from the first light source 100. The first illumination optical system 200A includes a first condensing lens 210, a first pair of positive and negative cylinder lenses, so-called variable cylinder lens 220a, and a first relay lens 220b.

As the first light source section 100, one having high space coherence and low time coherence is desirable. Here, as an example, an SLD is adopted as the first light source section 100, and a point light source with high brightness can be obtained. Incidentally, the first light source section 100 is not limited to the SLD, and even if coherence is high both in space and time like a laser, it can be used by inserting a rotating diffused plate or the like to suitably lower the time coherence. Even if coherence is not high both in space and time like an LED, if a light amount is sufficient, it can be used by inserting a pin hole or the like at a position of a light source in a light path. Besides, as the wavelength of the first light source section 100 for illumination, for example, a wavelength in an infrared range, for example, 780 nm can be used.

The first light receiving optical system 300A receives light flux reflected and returned from the retina 61 of the subject eye and passing through a second beam splitter 340, to guide it to the first light receiving section 510. The first light receiving optical system 300A includes a first afocal lens 310, a second variable cylinder lens 320a, a second relay lens 320b, the second beam splitter 340, and the conversion member 400 for converting the reflected light flux into at least 17 beams.

The conversion member 400 disposed in the first light receiving optical system 300A is a wavefront conversion member for converting the reflected light flux into plural beams. Incidentally, here, plural micro Fresnel lenses disposed in a plane orthogonal to an optical axis are adopted as the conversion member 400.

The first light receiving section 510 receives the light passing through the conversion member 400 from the first light receiving optical system 300A, to generate a first signal. With respect to the first light receiving section 510, the eyeground 61 and the first light source section 100 are conjugated, and the eyeground 61 and the first light receiving 510 are conjugated. Further, the conversion member 400 and the pupil are also conjugated. That is, a front side focal point of the first afocal lens 310 is substantially consistent with the pupil of the anterior eye part 62 of the subject eye as an object to be tested. The reflected light from the eyeground 61 passes through the first afocal lens 310 and the relay lens 320, and is condensed on the first light receiving section 510 through the conversion member 400.

The first illumination optical system 200A and the first light receiving optical system 300A are constructed such that they are moved together while maintaining such relation that on the assumption that light flux from the first light source 100 is reflected at a point where it is condensed, a signal peak at the first light receiving section 510 by the reflected light becomes maximum, and they are moved in the direction in which a signal peak at the first light receiving section 510 becomes high, and are stopped at a position where the strength becomes maximum. Alternatively, they are constructed to be moved according to a movement amount calculated on the basis of the refractive power calculated from a ring image obtained at the second light receiving section 520. As a result, the light flux from the first light source section 100 is condensed on the subject eye 60.

Besides, the first condensing lens 210 converts the diffusion light of the first light source section 100 into parallel light. A diaphragm 210a is located at a position optically conjugated to the pupil of the subject eye 60 or the conversion member (Hartmann plate) 400. The diaphragm 210a has a diameter smaller than the effective range of the Hartmann plate 400, so that so-called single path aberration measurement (method in which aberration of an eye has an effect only on a light receiving side) can be realized. The first relay lens 220b is arranged such that in order to satisfy the above, an eyeground conjugated point of a solid light beam is consistent with the front side focal position, and further, in order to satisfy the conjugated relation to the pupil of the eye, the rear side focal position is consistent with the diaphragm 210a.

Besides, the incident light beam emitted from the first light source section 100 comes to have a light path common to the measurement light beam diffused and reflected from the eyeground 61 at the second beam splitter 340, and then, advances in the same way as the measurement light beam diffused and reflected from the eyeground 61 in an approximate axis. However, at the time of single path measurement, the diameters of the respective light beams are different from each other, and the beam diameter of the incident light beam is set to be rather small as compared with the measurement light beam. Specifically, the beam diameter of the incident light becomes approximately 1 mm at the pupil position of the subject eye 60, and the beam diameter of the measurement light beam can be approximately 7 mm.

The second illumination optical system 200B is for illuminating a predetermined area on the retina of the subject eye with the second light flux from the second light source section 110. The second light source section 110 is for emitting the light flux with the second wavelength of, for example, 860 nm. The second illumination optical system 200B includes, for example, the second light source section 110, a third condensing lens 230, a first draw ring 240, a fourth condensing lens 250, a second draw ring 260, a lens 270, and a first beam splitter 330. The third condensing lens 230 and the first draw ring 240 are for illuminating the pupil, and the fourth condensing lens 250 and the second draw ring 260 are for illuminating the eyeground 61.

The second light receiving optical system 300B includes, for example, the first afocal lens 310, the first beam splitter 330, a beam splitter 345, and a second condensing lens 350. The structure is such that the light with the second wavelength reflected by a beam splitter 280 formed between the first beam splitter 330 and a beam splitter 285 is guided to the second light receiving section 520 through the first beam splitter 330 and the second condensing lens 350. The second light receiving section 520 generates a second signal. The beam splitter 285 is constituted by, for example, a dichroic mirror for reflecting the light flux with the first wavelength and permitting the light flux with the second wavelength to pass through.

Besides, a rotary prism 332 for unifying the light subjected to uneven reflection from the eyeground 61 is disposed between the second beam splitter 340 and the beam splitter 285. Similarly, a rotary prism 331 is disposed between the first beam splitter 330 and the beam splitter 280. The rotary prisms 331 and 332 become conjugated, and the pupil and the rotary prisms 331, 332 have a substantially conjugated relation.

The first light source 100, the second draw ring 260 equivalent to the second light source of the second light source section 110, and the eyeground 61 are conjugated, and the eyeground 61 and the first light receiving section 510, the second light receiving section 520 are conjugated. Further, the conversion member 400 and the pupil are also conjugated, and the pupil and the first draw ring 240 are conjugated.

The third light receiving optical system 30 includes relay lenses 31, 32, and 33, a telecentric diaphragm 34, and a third light receiving section (here, for example, an anterior eye part observing CCD) 35. The third light receiving optical system 30 guides light flux in which a pattern of a placido ring 41 illuminated from a light source section included in the first adjusting optical system 50 is reflected and returned from the anterior eye part 62 of the subject eye 60, to the third light receiving section 35. The telecentric diaphragm 34 is a diaphragm for preventing an image of the anterior eye part from blurring. The pupil and the telecentric diaphragm 34 are conjugated.

The first adjusting optical system 50 is, for example, mainly carries out a working distance adjustment, and includes light source sections 51 and 55, condensing lenses 52 and 53, and a light receiving section 54. Here, the working distance adjustment is carried out such that for example, parallel light flux in the vicinity of the optical axis emitted from the light source section 55 is irradiated toward the subject eye 60, and the light reflected from the subject eye 60 is received by the light receiving section 54 through the condensing lenses 52 and 53. Besides, in the case where the subject eye 60 is in a suitable working distance, a spot image from the light source section 55 is formed on the optical axis of the light receiving section 54. On the other hand, in the case where the subject eye 60 deviates from the suitable working distance in a front or rear direction, the spot image from the light source section 55 is formed at an upper or lower place with respect to the optical axis of the light receiving section 54. Incidentally, since the light receiving section 54 has only to detect the change of the light flux position on a plane containing the light source 55, the optical axis, and the light receiving section 54, for example, one-dimensional CCD disposed on this plane, a position sensing device (PSD) or the like can be applied.

The third illumination optical system 90 includes, for example, a light path for projection of an index to cause fixation of the subject eye or fogging, and includes the third light source section (for example, a lamp) 91, a fixation index 92, and a relay lens 93. The fixation index 92 can be irradiated to the eyeground 61 by the light flux from the third light source section 91, and the subject eye 60 is urged to observe the image. The fixation index 92 and the eyeground 61 are conjugated.

Figure 2:
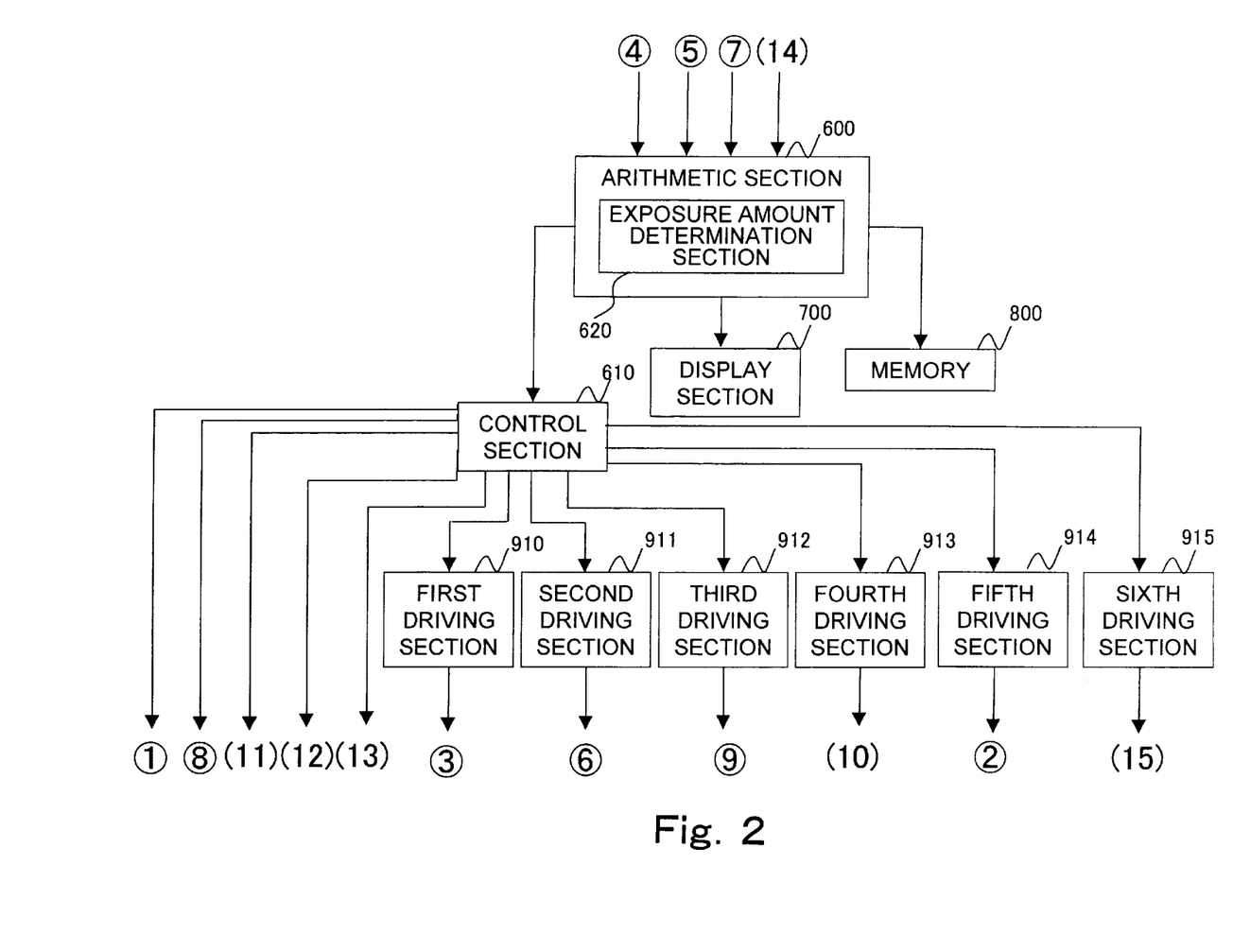
FIG. 2 is an electrical system block diagram showing an electrical structure of the ophthalmic characteristic measuring apparatus 1000 of the invention.

FIG. 2 is an electrical system block diagram showing an electrical structure of the ophthalmic characteristic measuring apparatus 1000 of the invention.

An electric driving system relating to the ophthalmic characteristic measuring apparatus 1000 includes an arithmetic section 600, a control section 610, a display section 700, a memory 800, a first driving section 910, a second driving section 911, a third driving section 912, a fourth driving section 913, a fifth driving section 914, and a sixth driving section 915. The arithmetic section 600 includes an exposure amount determination section 620 for adjusting an exposure time on the basis of the output of the first light receiving section 510 and/or the second light receiving section 520, an imaging state change section for changing a state when a wavefront measurement is carried out, and a measurement section for carrying out various ophthalmic characteristic measurements. The exposure amount determination section 620 determines exposure amount such as exposure time, light amount of light source, both exposure time and light amount of light source and so on.

Besides, the arithmetic section 600 is constructed so as to receive a first signal [4] from the first light receiving section 510, a second signal [5] from the second light receiving section 520, a signal [7] from the third light receiving section 35, and a signal (14) from the light receiving section 54. The arithmetic section 600 obtains the optical characteristics of the subject eye 60 on the basis of the first signal [4] from the first light receiving section 510, and carries out an operation of refractive power, astigmatic power, and astigmatic axis angle, and detects an illumination state of the first illumination optical system 200A on the basis of the second signal [5] from the second light receiving section 520. Besides, the arithmetic section 600 outputs signals corresponding to the arithmetic results to the control section 610 for performing the whole control of the electrical driving system, the display section 700 (various display examples are described later), and the memory 800.

The arithmetic section 600 obtains the optical characteristics of the subject eye 60 on the basis of the first signal from the first light receiving section 510 corresponding to a tilt angle of the light flux, and carries out the operation of refractive power, astigmatic power, and astigmatic axis angle and detects the illumination state of the first illumination optical system 200A on the basis of the second signal from the second light receiving section 520.

The imaging state change section changes the imaging state of the first illumination optical system 200A and the first light receiving optical system 300A into a first change state in accordance with the level of the second signal [5] from the second light receiving section 520, and then, changes the imaging state of the first illumination optical system 200A and the first light receiving optical system 300A into a second change state in accordance with the optical characteristics obtained by the arithmetic section 600. Incidentally, here, although the first wavelength is set to be shorter than the second wavelength, the reverse relation may be adopted.

On the basis of the control signal from the arithmetic section 600, the control section 610 controls lighting and extinction of the first light source section 100, and controls the first driving section 910 to the sixth driving section 915. On the basis of the signals corresponding to the arithmetic results of the arithmetic section 600, the control section 610 outputs, for example, a signal [1] to the first light source 100, outputs a signal (12) to the second light source section 110, outputs a signal (11) to the third light source section 91, outputs a signal (13) to the light source section 55, outputs a signal [8] to the light source section 51, and outputs signals to the first driving section 910 to the sixth driving section 915.

The first driving section 910 is for moving the first illumination optical system 200A and the first light receiving optical system 300A in the optical axis direction on the basis of the light receiving signal [4] inputted to the arithmetic section 600 from the first light receiving section 510, outputs a signal [3] to not-shown suitable lens movement means, and drives the lens movement means.

The second driving section 911 moves the second light receiving optical system 300B in the optical axis direction on the basis of the light receiving signal [5] inputted to the arithmetic section 600 from the second light receiving section 520, outputs a signal [6] to not-shown suitable lens movement means, and drives the lens movement means.

The third driving section 912 moves the second illumination optical system 200B in the optical axis direction on the basis of the signal (12) outputted to the second light source section 110 from the arithmetic section 600, outputs a signal [9] to not-shown suitable lens movement means, and drives the lens movement means.

The fourth driving section 913 is for rotating, for example, the rotary prisms 331 and 332, outputs a signal (10) to not-shown suitable lens movement means, and drives the lens movement means.

The fifth driving section 914 outputs a signal [2] on the basis of the signal [4] inputted to the arithmetic section 600 from the first light receiving section 510 or the signal [5] from the second light receiving section 520, to rotate the first cylinder lens 220a of the first illumination optical system 200A and the second cylinder lens 320a of the first light receiving optical system 300A. The fifth driving section 914 is constructed to drive suitable lens movement means to rotate the first cylinder lens 220a.

Incidentally, the suitable lens movement means in the fifth driving section 910 corresponds to the imaging state change section for changing the imaging state of the first illumination optical system 200A and the first light receiving optical system 300A.

The sixth driving section 915 is for moving the fixation index 92 of the third illumination optical system 90, outputs a signal (15) to not-shown suitable movement means, and drives this movement means. By this, the sixth driving section 915 can move and adjust the fixation index 92 of the third illumination optical system 90.

(Flowchart of a First Embodiment)

Figure 3:
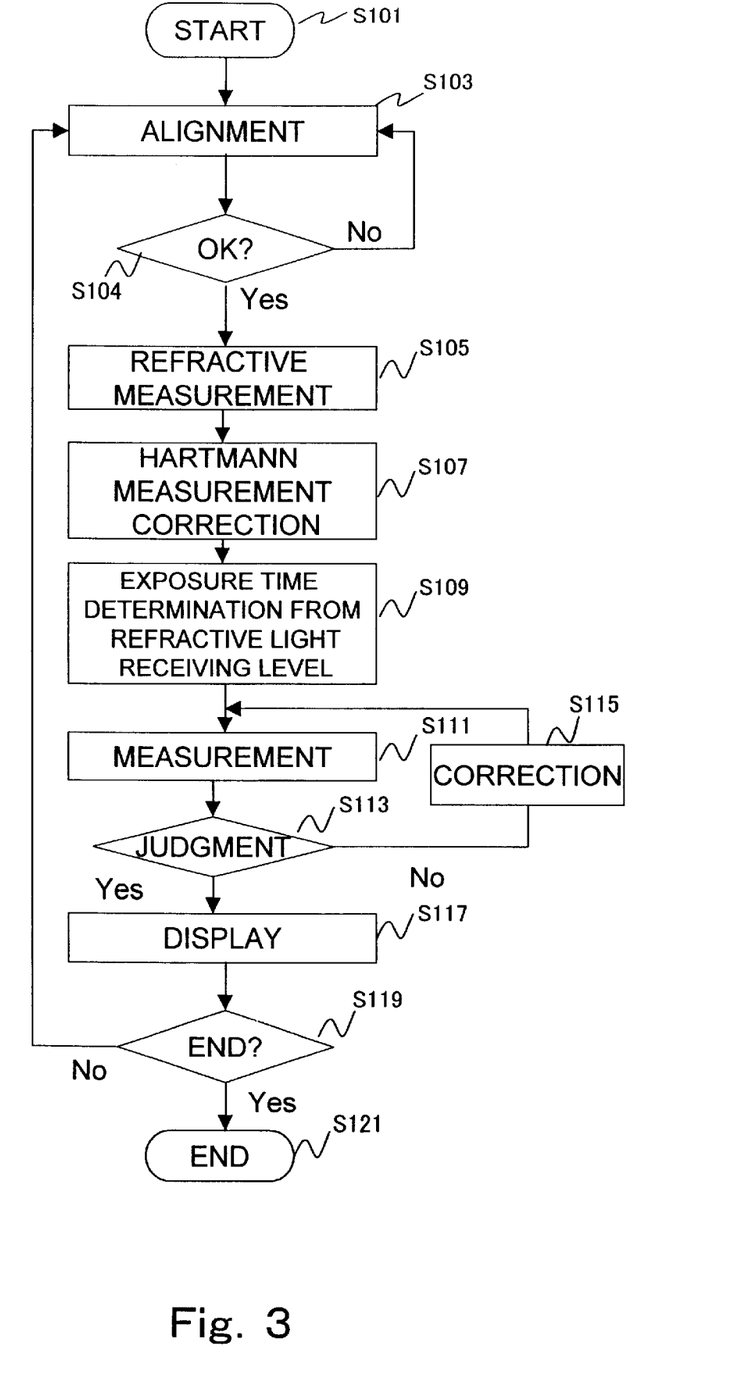
FIG. 3 is a flowchart of a first embodiment showing a specific measurement method of the ophthalmic characteristic measuring apparatus 1000.

FIG. 3 is a flowchart of a first embodiment showing a specific measurement method of the ophthalmic characteristic measuring apparatus 1000.

When a measurement is started (S101), first, an alignment adjustment of a position of the subject eye 60 is carried out (S103). Here, for example, the control section 610 controls a predetermined driving section on the basis of the control signal from the arithmetic section 600, and carries out an alignment in the XY direction and the Z direction to bring the subject eye 60 and the optical system of the ophthalmic characteristic measuring apparatus 1000 into a suitable arrangement (S103).

Next, it is judged whether or not the alignment adjustment at the step S103 is suitable (S104), and in the case where the alignment adjustment is suitable, a refractive measurement is executed (S105). On the other hand, in the case where the alignment adjustment is not suitable at the step S104, the processing is again returned to the step S103. The refractive measurement is such that the light flux from the second light source 110 is illuminated to the pupil or the eyeground by the second illumination optical system 200B, and detects the second light flux reflected and returned from the retina 61 of the subject eye through the second light receiving optical system 300B by the second light receiving section 520. On the other hand, the reflected ring image is detected by the second light receiving section 520. Incidentally, at this time, the first draw ring 240 is conjugated to the pupil, and similarly, the second draw ring 260 is conjugated to the eyeground.

Figure 4:
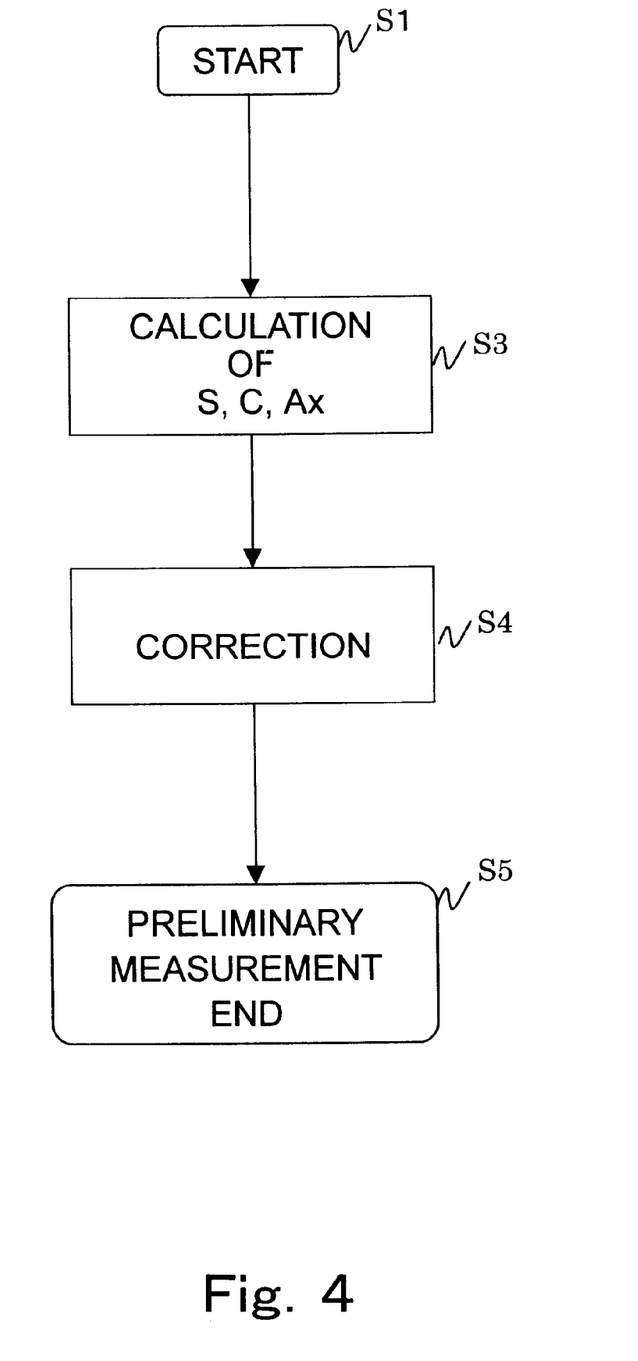
FIG. 4 is a flowchart concerning refractive measurement.

FIG. 4 is a flowchart of the refractive measurement.

Here, when the refractive measurement processing of the step S105 is started (S1), on the basis of the ring image detection result of the refractive measurement, the arithmetic section 600 carries out an operation of refractive power, astigmatic power, and astigmatic axis angle (S, C, Ax) (S3). Next, in accordance with the refractive power, the astigmatic power, and the astigmatic axis angle (S, C, Ax) calculated at the step S3 by the arithmetic section 600, the imaging state change section is controlled, and an illumination condition and a light receiving condition are corrected (S4). At the step S4, after the illumination condition and the light receiving condition are corrected, the refractive measurement is ended (S5). Here, on the basis of the refractive power, the astigmatic power, the astigmatic axis angle (S, C, Ax), movable portions are moved by the first driving section 910, the second driving section 911, and the third driving section 912.

Now, returning to FIG. 3 again, the description will be given.

When the refractive measurement at the step S105 is completed, a Hartmann measurement correction is executed (S107).

Next, the exposure amount determination section 620 of the arithmetic section 600 determines the exposure time from the refractive light receiving level measured at the step S105 (S109).

Here, the determination of the exposure time of the step S109 will be complementarily described.

With respect to the ring image of the refractive measurement by the second light receiving section 520 and the Hartmann image of the Hartmann measurement by the first light receiving section 510, if γ characteristic of a light receiving element such as a CCD is made 1 and a correction is carried out, a time and an amount of light are linear, and the relation of the respective exposure times can be regarded as substantially linear.

The ring image and the point light source for the Hartmann measurement are different in the impingement portion on the eyeground 61. That is, although uneven reflection exists on the eyeground 61, if minute movement is made on the eyeground 61 by the rotary prisms 331 and 332, etc., it is supposed that they are consistent with each other anywhere to a certain degree.

In accordance with the exposure time determined at the step S109, an eye characteristic measurement such as Hartmann wavefront measurement is carried out by the first light receiving section 510 (S111). At this time, for the purpose of determining the exposure time, as a pre-measurement, the Hartmann image is acquired with the exposure time determined by the refractive measurement, and if it is not suitable for the measurement, the exposure time may be corrected.

Figure 5:
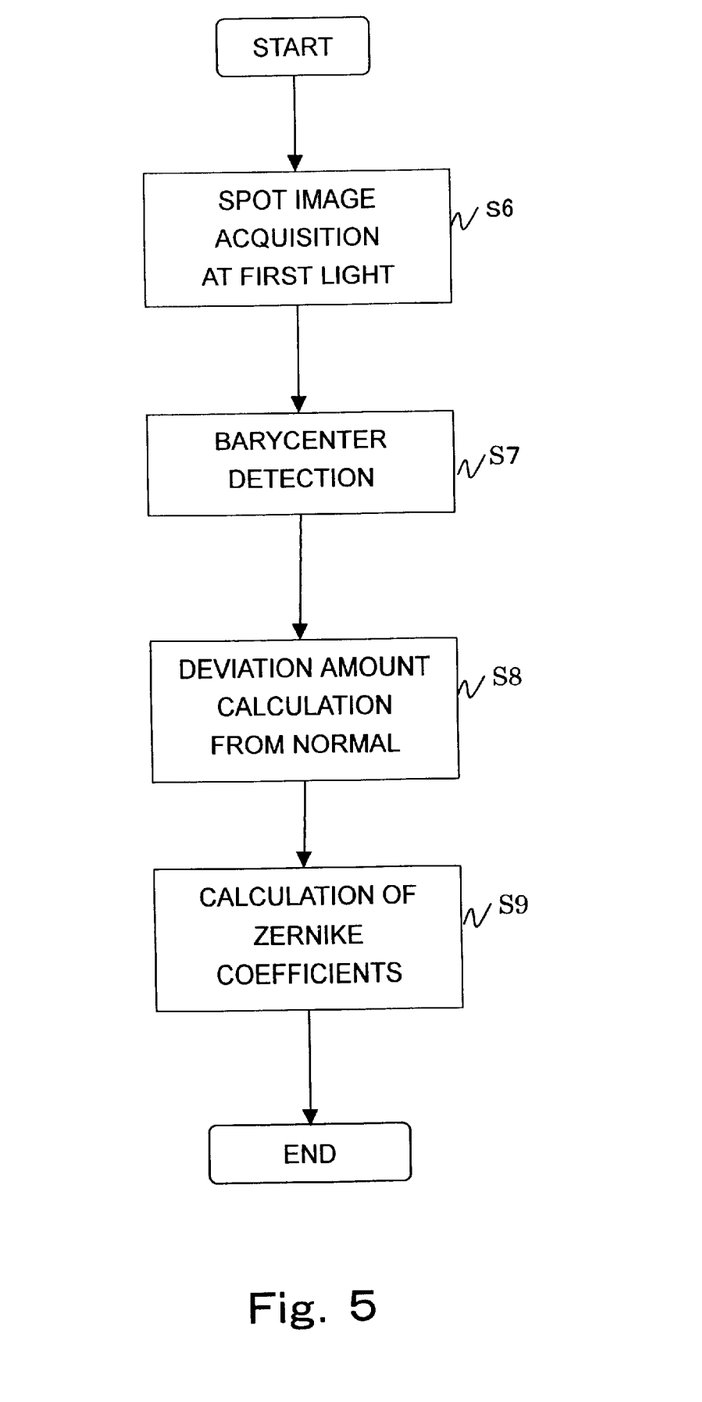
FIG. 5 is a flowchart concerning Hartmann measurement.

FIG. 5 shows a flowchart concerning the Hartmann measurement.

Specifically, for example, spot images are taken by the first light receiving section 510 (S6), and further, barycentric positions of the respective spots are detected (S7). With respect to the barycentric position, for example, the projected light flux is made to be projected on plural pixels on the light receiving surface, and the barycentric position can be obtained with reference to the intensity of the light flux of each of the pixels. By carrying out the barycentric calculation in this way, the measurement position accuracy of not more than 1/10 of the element can be ensured. Next, an amount of deviation from a normal barycentric position is calculated (S8). Further, Zernike coefficients are calculated (see Japanese Patent Laid-Open No. 2001-204690) (S9).

Next, it is judged whether or not the measurement result measured at the step S111 is suitable as a measurement value (S113).

For example, the arithmetic section 600 can judge the propriety as follows:

Whether or not a previously determined minimum requirement number of data are obtained?

Whether or not a measurement level is in a predetermined range?

Whether or not there is an abnormal (deviating from expectations extremely) measurement value?

In the case where the measurement value is not suitable at the step S113, the exposure time is corrected on the basis of the first signal (S115).

Besides, in the case where it is suitable as the measurement value at the step S113, the arithmetic section 600 displays the refractive power, the astigmatic power, the astigmatic axial angle, and other high-order aberration components (S, C, Ax, SA, Coma, . . . ) on the display section 700 (S117). Incidentally, if circumstances require, the results of a coarse measurement or a first measurement can be used.

Then, it is judged whether or not the measurement is to be ended (S119), and in case of end, the measurement is ended (S121). On the other hand, in the case where the measurement is not ended at the step S119, the processing is again returned to the step S103, and the alignment adjustment is carried out.

In the foregoing, although the embodiment has been described in which the exposure time is changed in order to change the exposure amount, the exposure amount determination section 620 may be constructed such that, instead of the exposure time, the light amount of the first light source section 100 or the second light source 110 is changed by the control section 600, and the amount of received light at the light receiving section is adjusted by the change of the light amount of the light source. Also, the exposure amount determination section 620 may be constructed such that the section adjusts both exposure time and light amount of light source.

(Flowchart of a Second Embodiment)

Figure 6:
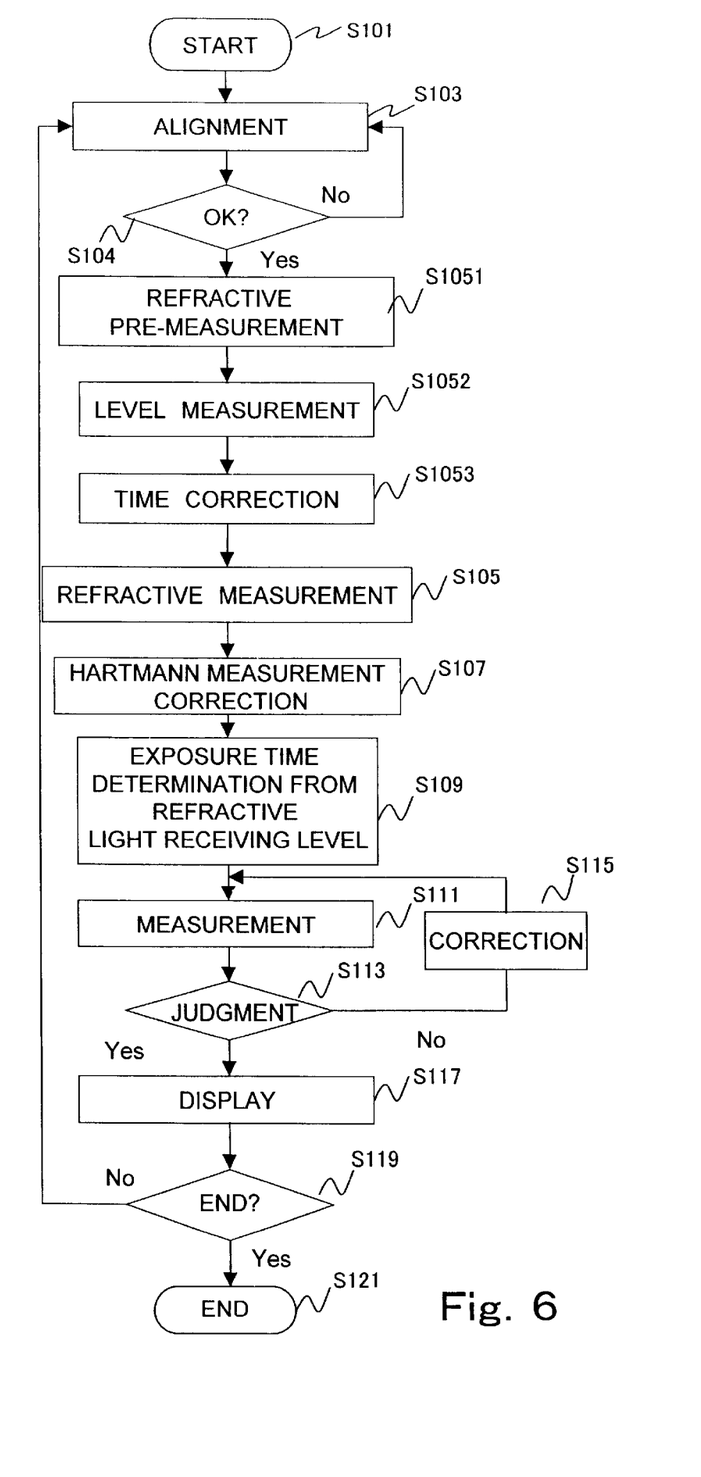
FIG. 6 is a flowchart of a second embodiment showing a specific measurement method of the ophthalmic characteristic measuring apparatus 1000.

FIG. 6 is a flowchart of a second embodiment showing a specific measurement method of the ophthalmic characteristic measuring apparatus 1000. Incidentally, a processing etc. overlapping with the foregoing flowchart (1) is denoted by the same symbol, and the function is the same.

When the processing is started, similarly to the above, an alignment adjustment is executed (S103), and in the case where it is suitable, as a refractive pre-measurement, a ring image from the second light source 110 of the second illumination optical system 200B, reflected by the eyeground 61 of the subject eye 60 and received by the second light receiving section 520 of the second light receiving optical system 300B, is acquired (S105). Next, the arithmetic section 600 measures the refractive light receiving level (level of the ring image) received at the second light receiving section 520 in the step S1051 (S1052). Next, in order to prevent the refractive exposure time from being put in a saturated state or becoming excessively small, a time correction is carried out (S1053). Incidentally, this time correction may be carried out by a linear operation, or may be suitably determined by the arithmetic section 600 on the basis of light receiving characteristics of the first light receiving section 510 and the second light receiving section 520 stored in the memory 800 etc. in advance. Thereafter, the arithmetic section 600 performs the processings of the step S105 to S121 as described above.

(Flowchart of a Third Embodiment)

In the first embodiment, the exposure time of the first light receiving section 510 for carrying out the Hartmann wavefront measurement is determined on the basis of the amount of the received light at the second light receiving section 520 at the time of the refractive measurement. On the other hand, in the third embodiment, the structure is changed such that a coarse measurement and a precise measurement are carried out in the first light receiving section 510 for carrying out the Hartmann wavefront measurement, and the exposure time of the first light receiving section 510 for carrying out the Hartmann wavefront measurement at the time of the precise measurement is determined on the basis of the light amount of received light at the first light receiving section 510.

Figure 7:
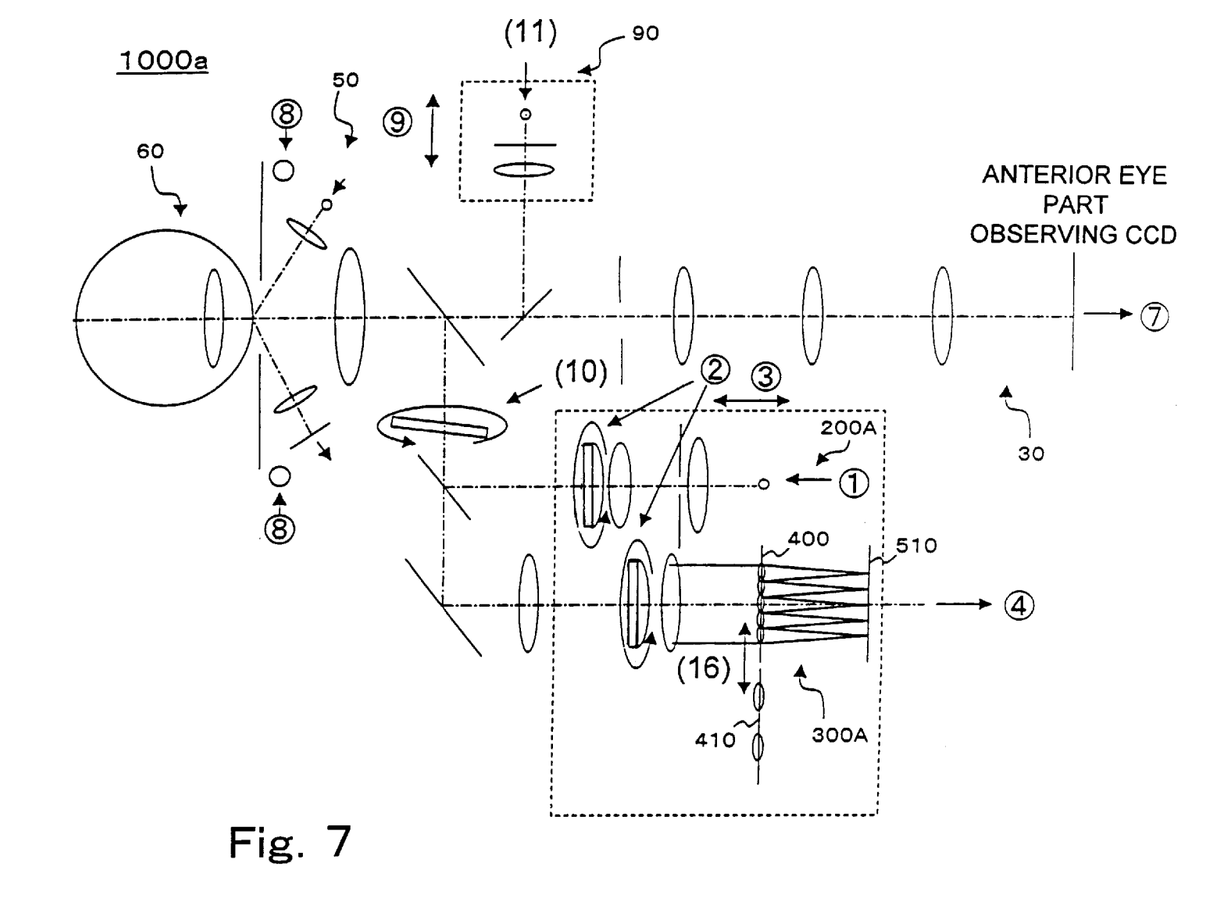
FIG. 7 is a view showing a general optical system of an ophthalmic characteristic measuring apparatus 1000a of the invention.

FIG. 7 is a view showing a general optical system of an ophthalmic characteristic measuring apparatus 1000a of the invention. Incidentally, the optical arrangement of the ophthalmic characteristic measuring apparatus 1000a is basically the same as the structure of FIG. 1, and the explanation of the common portions is omitted, and further, symbols of the same components as those of FIG. 1 are omitted in the drawing, and only different points will be described.

The ophthalmic characteristic measuring apparatus 1000a is constructed such that for example, the structure for the refractive measurement, that is, the second illumination optical system 200B and the second light receiving optical system 300B are omitted from FIG. 1, and the conversion member arranged in front of the first light receiving section 510 is constructed such that a second conversion member 410 having four openings for the coarse measurement, and a first conversion member 400 provided with at least 17 openings used for the precise measurement can be exchanged. At the coarse measurement, a changeover to the second conversion member 410 is carried out, and at the precise measurement, a changeover to the first conversion member 400 is carried out. This exchange is carried out by the control section 610 (see (16) in FIG. 7). Incidentally, it is assumed that the number of openings of the first conversion member 400 is larger than the number of openings of the second conversion member 410.

Figure 8:
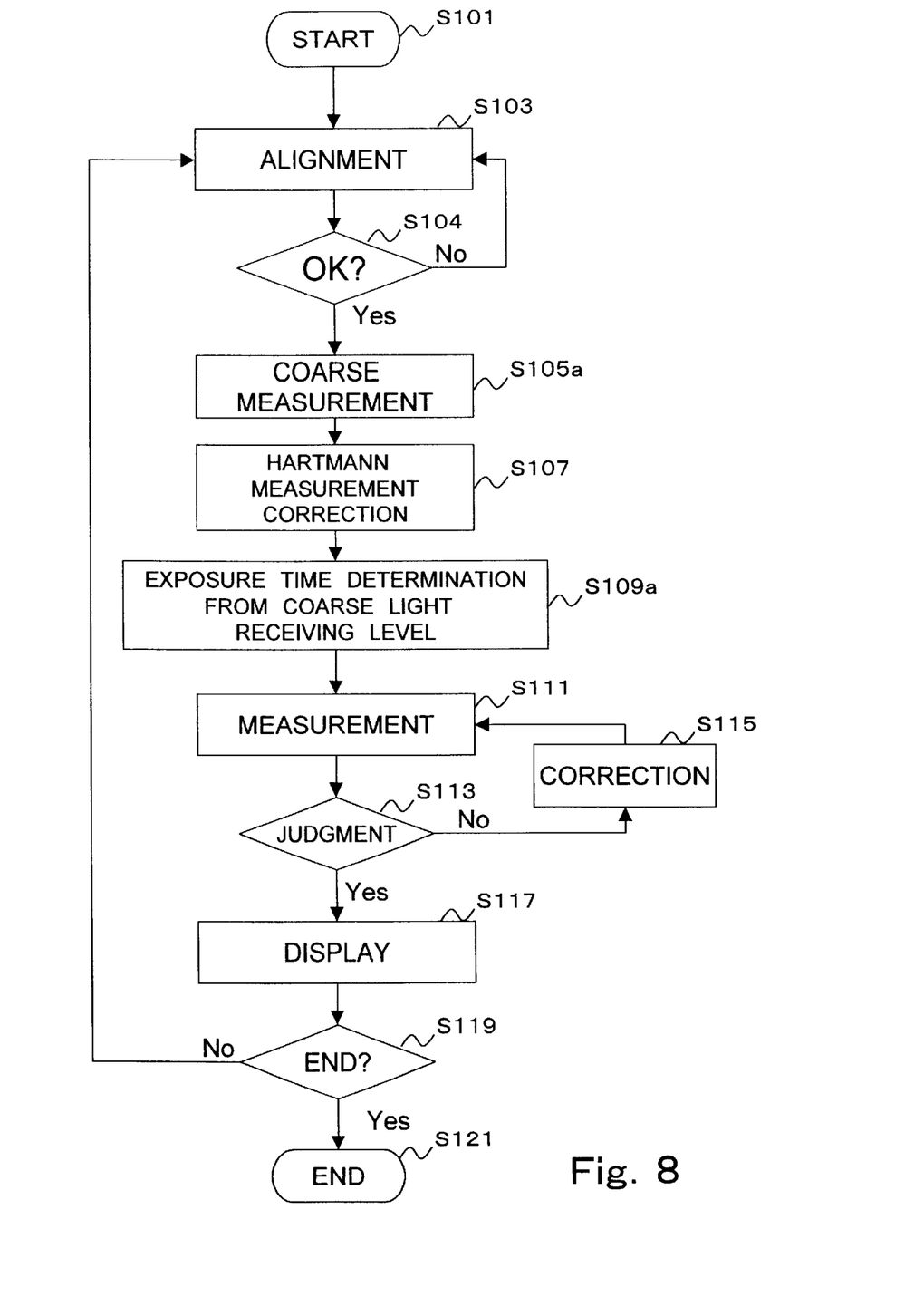

FIG. 8 is flowchart of the third embodiment showing a specific measurement method of the ophthalmic characteristic measuring apparatus 1000a. Incidentally, this flowchart is basically the same as the processing of FIG. 3, and the difference is that instead of the step of the refractive measurement of S105, a step of S105a is performed. Specifically, the second conversion member 410 for the coarse measurement of the Hartmann measurement is inserted in the light path, and the coarse measurement is carried out on the basis of the signal of the first light receiving section 510. At S107, the Hartmann measurement correction is carried out on the basis of the coarse measurement. At S107, the exposure time is determined on the basis of the image level of the first light receiving section 510 at the time of the coarse measurement.

Incidentally, although the structure is such that the conversion member is changed over, the structure may be such that separate components are provided and the light path is changed over. The coarse measurement is disclosed in Japanese Patent Application No. 2000-321509 previously filed.

(Flowchart of a Fourth Embodiment)

In the first to third embodiments, although the exposure time is determined on the basis of the light amount of the received light obtained at the time of the refractive measurement or the coarse measurement, in the fourth embodiment, for the time being, the Hartmann wavefront measurement (precise measurement·main measurement) is executed with the exposure time by default, and in the case where the measurement result is satisfactory and in the case where the measurement is not successively carried out, the measurement is ended as it is. In the case where the measurement is further continued, the exposure time is determined on the basis of the received light level of the first light receiving section 510 at the former measurement.

Figure 9:
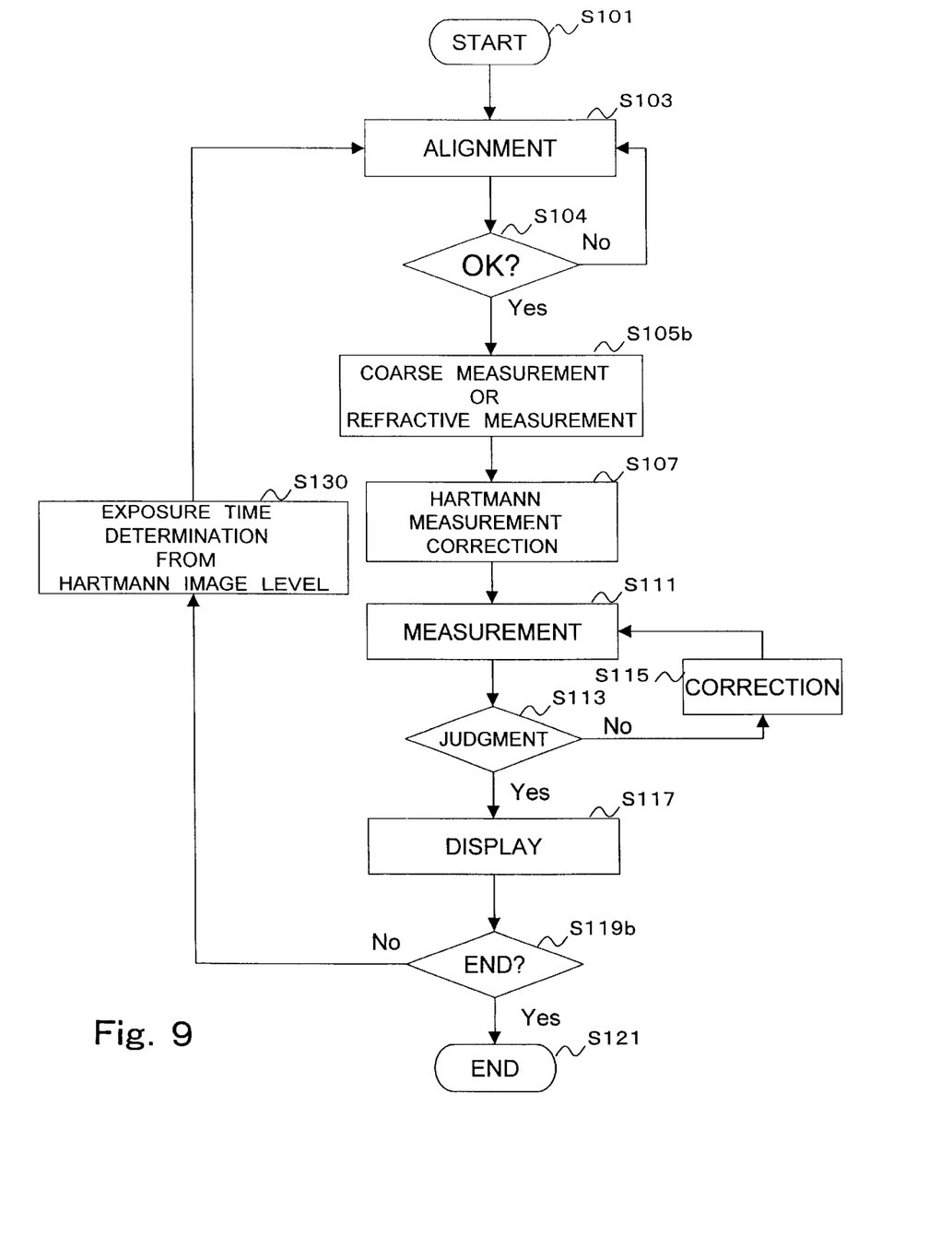

FIG. 9 is a flowchart of the fourth embodiment showing a specific measurement method of the ophthalmic characteristic measuring apparatus 1000a. Incidentally, this flowchart is basically the same as the processing of FIG. 3, and the difference is that instead of the step of S105 at which the refractive measurement is carried out, a step of S105b is carried out. Specifically, a coarse measurement or a refractive measurement of a Hartmann measurement is carried out. At S119b, the Hartmann wavefront measurement (precision measurement–main measurement) is executed with the exposure time by default, which was carried out at S111, and in the case where the measurement result is satisfactory and in the case where the measurement is not successively carried out, the measurement is ended as it is. In the case where the measurement is further continued, at S130, the exposure time is determined on the basis of the received light level of the first light receiving section 510 at the time of the former measurement.

The processing of S105b, that is, the refractive measurement or the coarse measurement is not carried out, but a movement may be made to a position where the Hartmann image can be suitably measured, for example, a position where the signal level of the Hartmann image reaches the peak.

(Display Example)

Figure 10:
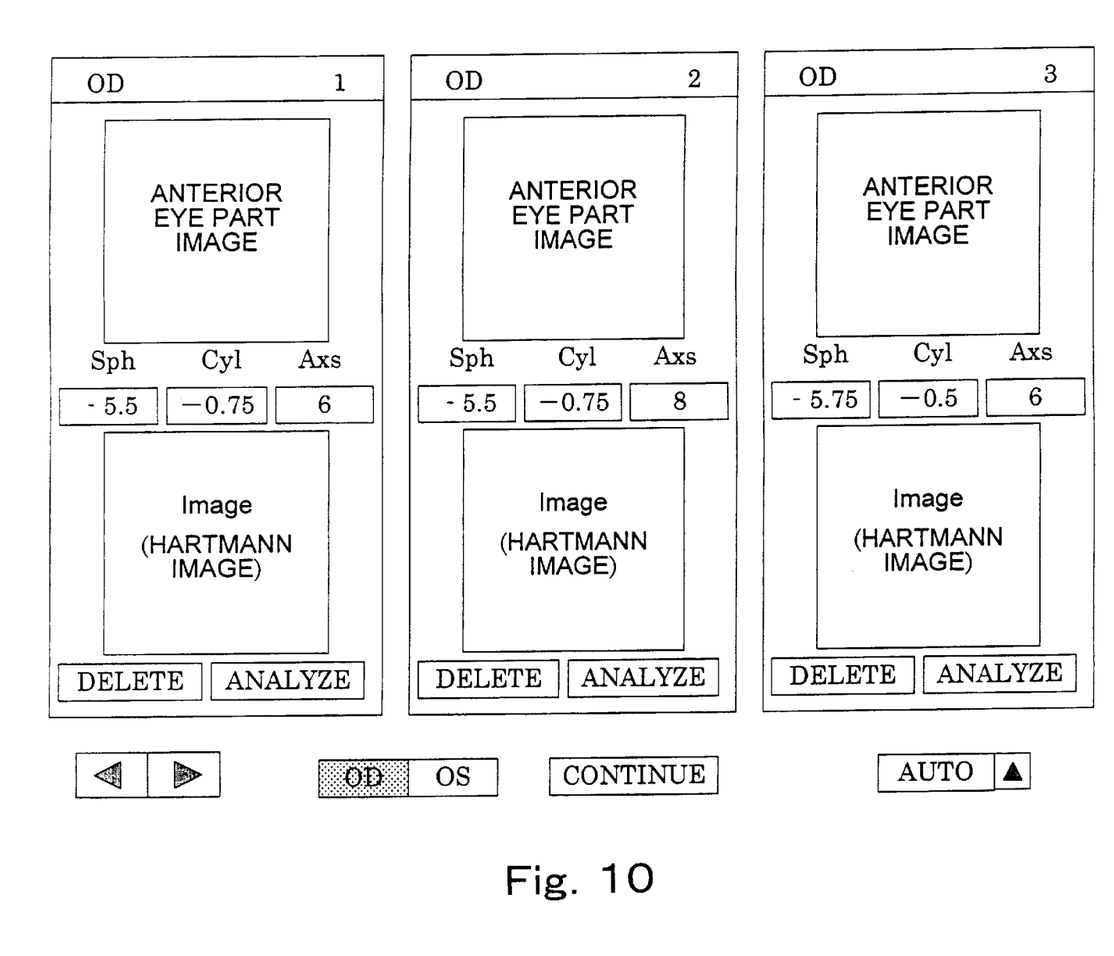
FIG. 10 is an explanatory view showing a display example graphic-displayed on a display section 700.

FIG. 10 is an explanatory view showing a display example graphic-displayed on the display section 700.

Here, there are shown states in which the first, the second, and the third of the display of measurement results are displayed on the display section 700 (for example, a display of a personal computer, etc.). On the display section 700, for example, an anterior eye part image, a Hartmann image, values of (S, C, Ax) as the measurement results by the refractive measurement are displayed.

In the drawing, [AUTO] is a mode setting button for determining the exposure time automatically or manually. That is, a proper user operates this mode setting button, so that in the case where setting of the exposure time described in detail at the step S109 is not carried out well, or in the case where a measurement with a different light amount or exposure time is desired to be carried out, manual setting can be carried out. At this time, the exposure time may be directly inputted, or levels are determined to a certain degree, and selection may be made among them. At the time of the manual setting, in the exposure time determination processing at the step S109, the exposure amount determination section 620 of the arithmetic section 600 reflects the setting to determine the exposure time.

In the exposure amount determination, in the case where the level of a light amount of received light is small, a suitable signal can be obtained by gain adjustment of the light receiving section of a CCD or the like.

What is claimed is:

1. An ophthalmic characteristic measuring apparatus, comprising:
    a first light source section for emitting light flux with a first wavelength;
    a first illumination optical system for illuminating a minute area on a retina of a subject eye with the light flux from the first light source section;
    a first light receiving optical system for guiding a section of first reflected light flux reflected and returned from the retina of the subject eye to receive it through a first conversion member for converting the first reflected light flux into substantially at least 17 beams;
    a first light receiving section for receiving the received light flux of the first light receiving optical system to form a first signal;
    a second light source section for emitting light flux with a second wavelength;
    a second illumination optical system for illuminating an eyeground of the subject eye with the light flux from the second light source section and with a predetermined pattern;
    a second light receiving optical system for guiding second reflected light flux reflected and returned from the eyeground of the subject eye to receive it;
    a second light receiving section for receiving the received light flux of the second light receiving optical system to form a second signal;
    an arithmetic section for obtaining a wavefront of the light flux reflected from the subject eye on the basis of the first signal from the first light receiving section, and obtaining refractive power of the subject eye on the basis of the second signal from the second light receiving section; and
    an exposure amount determination section for determining an exposure amount of the first light receiving section on the basis of the second signal of the second light receiving section.

2. An ophthalmic characteristic measuring apparatus according to claim 1, wherein the exposure amount determination section determines an exposure time of the first light receiving section or a light amount of the first and/or the second light source sections on the basis of previously stored light receiving characteristics of the first light receiving section and/or the second light receiving section.

3. An ophthalmic characteristic measuring apparatus according to claim 1, wherein the exposure amount determination section determines an exposure time of the first light receiving section or the light amount of the first and/or the second light source sections on the basis of the second signal of the second light receiving section obtained by a former measurement.

4. An ophthalmic characteristic measuring apparatus according to claim 1, wherein the exposure amount determination section determines an exposure time of the first light receiving section or a light amount of the first and/or the second light source sections on the basis of data manually set.

5. An ophthalmic characteristic measuring apparatus according to claim 1, wherein, when a wavefront of the subject eye is obtained on the basis of the first signal from the first light receiving section, the arithmetic section judges whether or not data is sufficient for measurement, and in a case where the data is sufficient, it is outputted as a measurement result, and in a case where the data is insufficient, the exposure amount determination section determines an exposure time of the first light receiving section.

6. An ophthalmic characteristic measuring apparatus according to claim 5, wherein the arithmetic section carries out a judgment as to whether or not the data is sufficient for the measurement, on the basis of the number of the acquired data or a level of the data.

7. An ophthalmic characteristic measuring apparatus according to claim 1, characterized in that the first and the second light receiving sections include CCDs.

* * * * *